United States Patent [19]

Rasmussen

[11] Patent Number: 4,466,966

[45] Date of Patent: Aug. 21, 1984

[54] N-ARYL-N'-(1,4,5,6-TETRAHYDROPYRIMI-DIN-2-YL)UREAS FOR INTESTINAL DISORDERS

[75] Inventor: Chris R. Rasmussen, Ambler, Pa.

[73] Assignee: McNeilab, Inc., Fort Washington, D.C.

[21] Appl. No.: 159,986

[22] Filed: Jun. 16, 1980

[51] Int. Cl.³ .................... A61K 31/505; C07D 239/02
[52] U.S. Cl. .................................... 424/251; 544/330; 544/332
[58] Field of Search ................ 424/251; 544/330, 332

[56] References Cited

U.S. PATENT DOCUMENTS

| | | | |
|---|---|---|---|
| 2,762,742 | 9/1956 | O'Neill | 544/332 |
| 2,830,054 | 4/1958 | Hepworth | 544/330 |
| 3,168,520 | 2/1965 | Kleemann et al. | 544/332 |
| 3,759,921 | 9/1973 | Paget | 544/332 |
| 4,285,948 | 8/1981 | Rasmussen | 544/332 |

*Primary Examiner*—Donald G. Daus
*Assistant Examiner*—James H. Turnipseed

[57] ABSTRACT

N-(substituted phenyl)-N'-(1,4,5,6-tetrahydropyrimidin-2-yl)ureas and pharmaceutically-acceptable salts thereof are disclosed to be useful in relieving the symptoms associated with irritable bowel syndrome, and as anti-diarrheal agents.

12 Claims, No Drawings

N-ARYL-N'-(1,4,5,6-TETRAHYDROPYRIMIDIN-2-YL)UREAS FOR INTESTINAL DISORDERS

FIELD OF INVENTION

This invention relates to a method for relieving the symptoms associated with irritable bowel syndrome and a method for controlling diarrhea employing certain N-aryl-N'-(1,4,5,6-tetrahydropyrimidin-2-yl)ureas and to certain of said urea compounds per se.

BACKGROUND OF THE INVENTION

Irritable bowel syndrome is a functional disorder characterized primarily by abdominal pain, but also by diarrhea and constipation and like symptoms. It is believed that the pain associated with this syndrome is due to excessive sensitivity to distention of the bowel caused either by intestinal gas and/or fecal material. Treatments which would provide relief from the discomforts associated with such symptoms and/or the disorder which produce such symptoms are highly desirable.

BRIEF SUMMARY OF THE INVENTION

The present invention involves a method for relieving the symptoms associated with irritable bowel syndrome and a method for controlling diarrhea in animals having said syndrome or in animals having diarrhea, respectively, by administering to said animal in a pharmaceutically-acceptable carrier, a therapeutically-effective amount of a compound, or a pharmaceutically-acceptable salt thereof, having the formula:

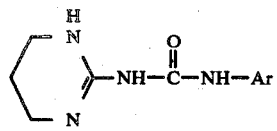

(I)

In the foregoing and subsequent formulas, Ar is a phenyl radical of the formula:

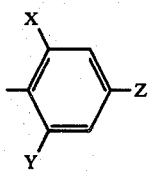

wherein X and Y are each independently selected from the group consisting of H, Br, Cl, F, $CH_3$, $CF_3$, or $OCH_3$; and Z is H or F.

The most preferred compounds, for use in relieving the symptoms associated with irritable bowel syndrome and as anti-diarrheal agents are those above wherein X and Y are each independently selected from the group consisting of Br, Cl, and $CH_3$ and Z is H.

This invention also involves, as compounds per se, the compound wherein X and Y are each Cl and Z is H, which is the most active compound for the above methods, and its pharmaceutically-acceptable salts, and the compound and its salts wherein X is Cl, Y is $CH_3$; and Z is H.

The activities of the above compounds reside in the urea base so that useful acid addition salts may be from various acids provided only that the acids be pharmaceutically-acceptable. Representative acid salts include hydrochloride, hydrobromide, phosphate, sulfate, p-toluenesulfonate, benzenesulfonate, malonate, succinate, methosulfate, methanesulfonate, 2-napsylate and the like.

PRIOR ART

Certain N-(aryl)-tetrahydropyrimidin-2-yl ureas are generically disclosed in U.S. Pat No. 3,168,520, but the only utility taught is in connection with dyeing, and no pharmaceutical utility is taught, nor is any of the compounds used in the present invention specifically disclosed.

An article by G. H. Douglas, et al., *Arzneimittel Forschung.*, Vol. 28 (II) Supplement 8a, 1435–1441 (1978) discloses as Compound 109 at p. 1438 (in its tautomeric form) the compound of the formula:

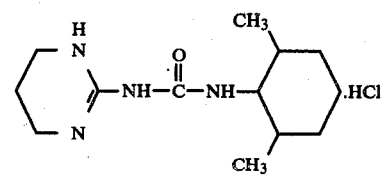

which was disclosed to be active as a gastric acid antisecretory agent. The article does not teach the activity as an anti-diarrheal agent or in relieving the symptoms associated with irritable bowel syndrome for this 2,6-dimethylphenyl compound, which applicant found to exist.

Method of Preparation

The pharmacologically useful N-aryl-N'-(1,4,5,6-tetrahydropyrimidine-2-yl)urea compounds are prepared from 2-amino-1,4,5,6-tetrahydropyrimidine.HCl, which has the structure:

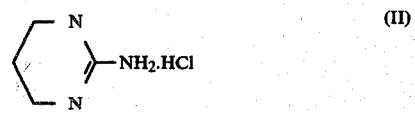

(II)

and which is a known compound (R. F. Evans and D. J. Brown, *J. Chem. Soc.*, 4039 (1962) prepared according to the following reaction scheme:

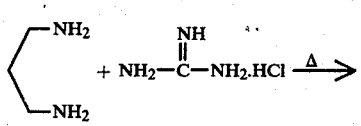

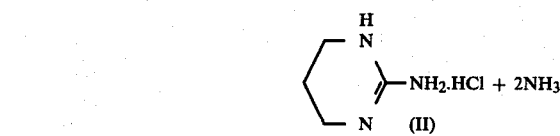

(II) $\xrightarrow{\text{base}}$ (II) free base + ArNCO $\xrightarrow{\text{solvent}}$ (III)

-continued

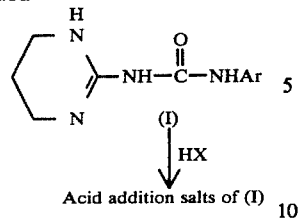

The free base form of II can be generated by treating a stirring suspension of II HCl in solvents such as CH$_2$Cl$_2$ (methylene chloride), tetrahydrofuran, dioxane, and the like with strong bases such as aqueous NaOH (50%), concentrated KOH, and the like; NaOH (50%) being preferred. The resulting solution of free base II is dried over a suitable drying agent such as Na$_2$SO$_4$ or K$_2$CO$_3$. The dried solutions may either be used as such for reactions with aryl isocyanates to obtain products I or the extraction solvent may be evaporated in vacuo and the residual free base II taken up in a different organic solvent, e.g., DMF, DMSO, and the like; said solutions of II then being treated with an appropriate isocyanate III to afford the free base products I. Although the reactions of II with III may be carried out with equimolar amounts of reactants, usually a stoichiometric excess, generally of from about 0.25-1.0 mole of free base II to that of aryl isocyanate III is employed in order to minimize undesired side reactions such as, for example, formation of bis-aryl isocyanate adducts with II. Temperature ranges for those reactions may conveniently range from about −20° to 70° C. The products I, obtained in free base form, may conveniently be purified by dissolving in an organic solvent, immiscible with H$_2$O, such as CH$_2$Cl$_2$, washing with H$_2$O to remove excess II, if any, followed by isolation of I from the solvent by drying, filtration from drying agent, and solvent removal.

Alternatively, the reactions of II free base with III may be carried out by adding a solution of II HCl in DMF, DMSO, and the like, to a stirring suspension of a stoichiometric amount of an alkali metal hydride such as LiH, NaH, and the like, LiH being preferred, which forms II free base, the corresponding alkali metal chloride, and H$_2$ gas. The thus obtained solution of free base II (the presence of the metal chloride does not interfere with the subsequent reaction) is treated with an appropriate amount of aryl isocyanate III. When the reaction is complete, dilution with H$_2$O or ice-H$_2$O, in excess amounts, causes precipitation of crude product I and leaves any unreacted II in solution. Filtration then allows isolation of crude I.

Said I, in free base form, may be further purified, if necessary, by recrystallization and chromatographic techniques, and so forth, according to standard techniques known in the art. A further purification method may be used such as dissolution in dilute aqueous acid, such as HCl, most preferred, H$_2$SO$_4$, HBr, HNO$_3$ and the like, filtration from any undissolved impurities, followed by neutralization with suitable inorganic bases such as sodium and potassium bicarbonates and carbonates and the like, dilute alkali metal hydroxides such as NaOH, KOH, and the like, and organic bases such as triethylamine, diisopropylethylamine, and the like, which causes precipitation of I free base. The thus-obtained free base I may then be purified by recrystallization, etc., as described above, or may be converted to a suitable pharmaceutically-acceptable salt form of I which also may be purified by recrystallization or precipitation techniques well known in the art.

Said pharmaceutically-acceptable salt forms of I are generally comprised of I in combination with suitable mineral acids such as HCl (most preferred), HBr, H$_2$SO$_4$, H$_3$PO$_4$, and strong organic acids such as benzenesulfonic, p-toluenesulfonic, 1- and 2-naphthalenesulfonic, ethanedisulfonic, methane- and ethanesulfonic methylsulfuric, and the like, being the most preferred. Although salts of I with weaker acids, such as benzoic, furmaric, maleic, citric, etc. do form, they are relatively easily dissociated because of the relatively weak base strength of I. This dissociation may be caused by attempted drying in vacuo, dissolution in H$_2$O, etc. The ease of dissociation, however, may not necessarily preclude use of salts of this type in pharmaceutical formulations insofar as they remain stable enough to be purified by recrystallization, etc. and capable of being formulated into pharmaceutical preparations such as tablets, capsules, and the like.

The preferred salt forms of I are additionally capable of forming hydrates and solvates with H$_2$O and certain organic solvents, respectively. Also, I and its salts forms may exist in several tautomeric forms. It is naturally intended that the various hydrates, solvates, and tautomeric forms of I be included within the scope of this invention.

The N-aryl-N'-(1,4,5,6-tetrahydropyrimidin-2-yl)urea compounds have been found to be useful as anti-diarrheal agents and to provide relief from the discomfort associated with functional intestinal disorders spoken of as irritable bowel syndrome. The disorder is characterized by abdominal pain, diarrhea, constipation and like symptoms caused by excessive sensitivity to distension of the bowel by the presence of intestinal gas and/or fecal material.

Definition of "irritable bowel syndrome"—this condition also known as irritable colon, spastic colon, mucous colitis, is a clinical disorder characterized by either diarrhea or constipation, in association with abdominal discomfort, but without demonstrable structural bowel disease. It is classified as a functional bowel disease.

In practice, it is one of the major digestive disorders and is a leading cause of absenteeism from work and a reason for physician office visits. In modern usage, "irritable bowel syndrome" is the preferred term for this condition.

Pathophysiology—Although the etiology is unknown, recent studies have elucidated characteristics of the pathophysiology of this condition. Alteration of colonic motility has been suggested as a mechanism of this syndrome. This is characterized by an increased basal activity, as well as a sensitivity to exogenous or endogenous stimuli. Since the symptoms many times are brought on by eating, it has been postulated that cholecystokinin, which is released from the small intestine after eating is partially responsible.

Electrical recordings from the human colon have also shown that there is a difference in the characteristic slow wave frequency in patients with irritable bowel.

Patients with irritable bowel syndrome have a lower pain threshold to distention than normal. Thus, they are much more sensitive to the distention caused by normal amounts of gas or fecal contents present in the colon. If the sensitivity to distention can be reduced, the pain associated with irritable bowel syndrome necessarily will be reduced.

Irritable bowel appears to be unique to man and no naturally-occurring disease similar to irritable bowel has been discovered in animals. In order to test compounds for possible activity in this state, the pathophysiologic characteristics of the disease must be utilized in designing animal experiments to test such compounds. The "glass bead test" described below has been developed to test for the effectiveness of compounds against one component of this disease state, that of response of the colon to distention, which could produce abdominal pain. Although no way of producing an increased sensitivity to distention of the bowel has been found in the mouse, stimulation by a greater than normal distending force is utilized. A drug interfering with this response to distention may be of use in the treatment of irritable bowel syndrome if it has other characteristics which could provide efficacy.

The "glass bead test" can also be used to evaluate antidiarrheal activity. Although most drugs producing constipation in man are effective in the glass bead test, many work by mechanisms which do not fulfill the characteristics of an agent which both decreases the response of an agent which both decreases the response to distention and effects abnormal motor activity. One example is that of narcotic analgesics which are effective in the glass bead test, but increase the phasic motor activity of the intestine and are not useful in irritable bowel. Other test models should, therefore, be used to confirm or further define the utility of any compound as an anti-irritable bowel agent.

One test to confirm the utility of compounds effective in the glass bead test, which may be used as an indicator of effectiveness for the diarrhea state produced by irritable bowel syndrome is the "castor oil diarrhea test" in mice or rats. (A description of this test is given infra.) The series of compounds for which there is claimed anti-irritable bowel activity in fact are active against castor oil diarrhea, the effective doses correlating well with those which are effective in the glass bead test.

Since there is no model for the constipation phase of this condition, the regularizing action of a compound cannot be examined. However, since constipation in irritable bowel syndrome is often secondary to diarrhea, one would expect that the prevention of diarrhea should alleviate the constipation phase.

The Glass Bead Test—The extent to which a compound is effective in providing relief from the symptoms associated with irritable bowel syndrome may be determined by a test in which a glass bead is inserted into the rectum and the lapse time between insertion and expulsion of the bead determined. Compounds which are effective in decreasing the sensitivity to distention of the colonic wall delays the expulsion of the bead.

The test is carried out with male albino mice of 18–25 grams body weight using groups of five mice for each compound dose tested. The initial screen dose selected for all compounds is 50 milligrams per kilogram of body weight (mg/kg) administered orally in a volume of 0.1 milliliter per 10 grams of body weight. The control groups receive the vehicle, 0.5 percent methocel, used for both oral and intraperitoneal administration. The mice are fasted one hour before testing and the test drugs are given one hour prior to glass bead insertion.

At the end of the pretreatment time, the mouse is picked up and held firmly in one hand with his abdomen facing the technician. The glass bead of 3 millimeters in diameter is positioned at the rectum and using a pinching action with a thumb and forefinger, the bead is pushed into the rectum. Then using a glass rod of 3 millimeters in diameter which has been lubricated with 0.5 percent methocel to facilitate insertion, the glass bead is pushed up into the rectum a distance of 2 centimeters using a slow gentle turning motion. The mice are timed as a group using the last mouse inserted as zero time and the number of beads expelled in a group at different timed intervals are recorded. The groups are based on timed intervals of 0 to 5 minutes, 5 to 10 minutes, 10 to 20 minutes, 20 to 40 minutes, and greater than 40 minutes. They are given the activity index values of 0, 1, 2, 3, and 4, respectively. Mice who have not expelled their beads by the 40-minute cutoff time are examined for perforations. Those mice whose colons are perforated are eliminated from the group. The sum of the values divided by the number of mice or beads is termed the activity index for the drug tested. The $ED_{50}$ is determined by regression lines using the method of last squares. The $ED_{50}$ is arbitrarily assigned as that dose causing an activity index of 2. The $ED_2$ is essentially equivalent to the $ED_{50}$, with the activity being expressed on a scale of 0 to 4 in the Glass Bead Test.

The results of this test employing intraperitoneal and oral administration of N-aryl-N'-(1,4,5,6-tetrahydropyrimidin-2-yl)urea compounds are shown in Table I. Table I also contains results of the Mouse Castor Oil Method Test described below.

TABLE I

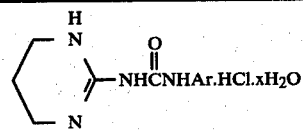

| | | | MOUSE | | |
|---|---|---|---|---|---|
| | | | n = 5–10 Glass Bead Test $ED_2$ P.O. | n = 5 Castor Oil Diarrhea Test mg/kg p.o. | |
| Ar | x | McN— | mg/kg | 1 hour | 5 hours |
| 2,6-Cl$_2$Ph | — | 4951(base) | 9.4 | 1.6 | 3.9($ED_{50}$) |
| 2,6-Cl$_2$Ph | 0 | 4951-11 | 7 mg/kg p.o. 4.3 mg/kg i.p. | | 6.5($ED_{50}$) |
| 2-CF$_3$Ph | 1 | 5027-11-98 | >200 | 100 | >100 200 lethal (4/5) |
| 2,6-Me$_2$Ph art compound | 1.1 | 5028-11-98 | 28.6 | <50 | 21.5($ED_{50}$) |
| 2-Cl—6-Me$_2$Ph | 0.5 | 5058-11-98 | <6.25 | — | 18 |

TABLE I-continued $$\left\langle \begin{array}{c} -N \\ \phantom{-}N \end{array} \right\rangle - NHCNHAr \cdot HCl \cdot xH_2O$$
(with H on top N and O double-bonded to C)

| | | | MOUSE | |
|---|---|---|---|---|
| | | | n = 5–10<br>Glass<br>Bead Test<br>$ED_2P.O.$ | n = 5<br>Castor Oil<br>Diarrhea Test<br>mg/kg p.o. |
| Ar | x | McN— | mg/kg | 1 hour   5 hours |
| 2,6-Br$_2$—4-F Ph | 0 | 5042-11 | >200 | 50        145 |

Mouse Castor Oil Method Test—Male albino mice weighing 18–30 gms are employed for this study. The mice are fasted overnight before testing; however, water is given ad lib. during fast. On the day of testing, the mice are weighed beforehand to obtain an average weight using an individual weight range of +5 gms.

Drugs are administered by the desired route (p.o., s.c., or i.p.) suspended or dissolved in 0.5 percent methocel using a volume of 1 ml/100 gm of average body weight (0.1 ml/10 gm) to groups of five mice for each compound dose tested. Control mice receive the test vehicle. One hour after, a single dose of castor oil (0.3 ml per mouse) is given orally to all groups. The mice are returned to their cages with access to food and water for the remainder of the experiment.

Mice fasted overnight will have diarrhea usually within one hour after administration of castor oil. Observations for the presence of diarrhea are taken every hour for five hours. A positive or negative response is used. The absence of diarrhea is expressed in percent inhibition as compared to the incidence of diarrhea at that time period in the control group. $ED_{50}$'s are determined by calculation regression analysis using a least square method. The effect over the total duration of the experiment is used for this calculation.

The foregoing results in Table I illustrate the beneficial effect of N-aryl-N'-(1,4,5,6-tetrahydropyrimidin-2-yl)urea compounds in decreasing abnormal sensitivity to distention of bowel. These properties are utilized in the methods and compositions of the present invention.

The process of the present invention, namely, a method for alleviating functional intestinal disorders and for treating the discomforts associated therewith comprises administering to subjects in need of treatment, a therapeutically-effective amount of an N-aryl-N'-(1,4,5,6-tetrahydropyrimidin-2-yl)urea compound of Formula I or its pharmaceutically-acceptable salt as active agent. The active agents may be administered with or without carrier in the amounts hereinafter set forth. A preferred method of administration is by use of pharmaceutical compositions in unit dosage form as described below.

The operable ranges for carrying out the process is the administration, orally or parenterally, of from about 1 milligram to about 500 milligrams of an N-aryl-N'-(1,4,5,6-tetrahydropyrimidin-2-yl)urea compound in dosage unit form. While the therapeutic method is most useful for human subjects, it may also be employed for other mammals. Operable amounts are generally within the range of from about 0.50 to 100 mg/kg.

The outstanding properties are most effectively utilized by use of the pharmaceutical compositions of the present invention. The pharmaceutical compositions comprising an N-aryl-N'-(1,4,5,6,-tetrahydropyrimidin-2-yl)urea compound or acid addition salt thereof, as the active ingredient, may be prepared by intimately mixing the urea compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are employed. If desired, tablets may be sugar-coated or enteric-coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonsful, tablespoonsful, and the like, and segregated multiples thereof. A dosage unit generally will contain from about 10 to about 500 mg of the N-aryl-N'-(1,4,5,6-tetrahydropyrimidin-2-yl)urea compounds.

The following examples illustrate the preparation of the urea compounds suitable in the practice of the invention, but are not to be construed as limiting.

EXAMPLE I-A

N-(2,6-Dichlorophenyl)-N'-(1,4,5,6-tetrahydropyrimidin-2-yl)urea

A solution of 4.20 g (0.0424 mol) of 2-aminotetrahydropyrimidine in 30 ml of dry DMF was warmed to 70° C. and with stirring there was added 7.16 g (0.0381 mol) of 2,6-dichlorophenyl isocyanate in 25 ml of dry DMF over a period of 0.5 hours. After stirring for 2 hours at 70° C., the reaction mixture was cooled, diluted with H₂O and filtered. The filter cake was washed well with H₂O and air dried. The crude product, 5.1 g (47%) was dissolved in CH₂Cl₂, dried over K₂CO₃, filtered through a prewashed pad of filter aid and hexane was added to the cloud point. The resulting crystals were filtered, washed with hexane and dried in vacuo for 3 hours (50° C.; 5 mm Hg) to give pure N-(2,6-dichlorophenyl)-N'-(1,4,5,6-tetrahydropyrimidin-2-yl)urea, 4.71 g (43%); m.p. 179°–180.5° C. TLC: 5×20 cm silica gel; toluene-ether-MeOH (8:4:1) or CHCl₃—MeOH—NH₄OH (90:10:1) indicated homogeneity; IR (KBr) 3421,1628 cm⁻¹; UV max. (MeOH) 222 nm (ε=28300) and 239 nm (inflection) (ε=18,000).

ANAL. Calcd. for C₁₁H₁₂Cl₂N₄O: C, 46.01; H, 4.21; N, 19.51. FOUND: C, 45.98; H, 4.23; N, 19.48.

The starting 2-aminotetrahydropyrimidine was prepared according to the procedure of R. F. Evans, D. J. Brown, *J. Chem. Soc.*, 4039 (1962), which was liberated from the hydrochloride with excess 50% NaOH, extracted with CH₂Cl₂, dried (K₂CO₃) and evaporated in vacuo to an oil.

EXAMPLE I-B

N-(2,6-Dichlorophenyl)N'-(1,4,5,6-tetrahydropyrimidin-2-yl)urea Monohydrochloride A mixture of 8.50 g (0.0625 mol) of 2-amino-1,4,5,6-tetrahydropyrimidine hydrochloride, 10.0 g (0.12 mol) of 50% NaOH and 70 ml of THF was stirred for 0.5 hours at room temperature and then 10.0 g Na₂SO₄ was added. After stirring for an additional 0.5 hours, a solution of 9.4 g (0.050 mol) of 2,6-dichlorophenyl isocyanate in 50 ml of THF was added over a period of 1 hour. After stirring for 1 hour, the reaction mixture was filtered, the filtrate evaporated in vacuo and the residue dissolved in 25 ml of 10% HCl and 25 ml of H₂O with warming. After filtration through a pad of diatomaceous earth, chilling in ice gave the crystalline hydrochloride which was recrystallized from MeOH-ether affording 12.40 g. This material was ground to a fine powder and dried to constant weight in vacuo (60° C., 5 mm Hg) to give 11.97 g (74%) of the title compound; m.p. 215°–217° C. dec., homogeneous by TLC [5×20 cm silica gel GF CHCl₃—MeOH-NH₄OH (90:9:1)]. ¹H-NMR (DMSO-d₆) 1.85 [pentet, (poorly resolved)2H]; 3.35 (t, J=5 Hz, 4H); 7.2–7.7 (m, 3H); 9.16 (broad s, 2H) exchangeable; 10.02 (broad s, 1H) exchangeable, 11.19 (brS, 1H) exchangeable. IR(KBr) 3125, 1717, 1678, 1678 cm⁻¹; UV max. (MeOH) 241 infl. (ε=11,200) and 220 nm infl. (ε=23,500).

ANAL. Calcd. for C₁₁H₁₂Cl₂N₄O.HCl: C, 40.83; H, 4.05; N, 17.31. FOUND: C, 4078; H, 4.05; N, 17.30.

EXAMPLE II

N-(1,4,5,6-tetrahydropyrimidin-2-yl)-N'-(2-trifluoromethylphenyl)urea Monohydrochloride Hydrate A mixture of 9.90 g (0.073 mol) of 2-amino-1,4,5,6-tetrahydropyrimidine hydrochloride, 6.0 g (0.075 mol) of 50% NaOH and 75 ml of THF was stirred for 0.75 hours at room temperature and then 10 g. Na₂SO₄ was added. After stirring for 0.5 hours, a solution of 9.36 g. (0.050 mol) of methyl-2-trifluoromethylphenyl isocyanate in 50 ml of THF was added over a period of 0.5 hours. After stirring for 1 hour, the reaction mixture was filtered, the filtrate evaporated in vacuo and the residue dissolved in 50 ml of 10% HCl and 100 ml of H₂O with warming. After filtration through a pad of diatomaceous earth, chilling in ice gave the crystalline hydrchloride which was recrystallized from hot H₂O affording 10.09 g (63%). This material was dried to constant weight in vacuo (20° C., 5 mm Hg) to give pure N-(1,4,5,6-tetrahydropyrimidin-2-yl)-N'-(2-trifluoromethylphenyl)urea monohydrochloride hydrate; m.p. (120) 182.5°–184.5° C. IR(CHCl₃) 3240 (br), 1717, 1642, 1594 cm⁻¹; UV max. (MeOH) 281 infl (ε6,900), 256 nm (ε29,000) and 215 nm (ε14,900).

ANAL. Calcd. for C₁₂H₁₃F₃N₄O.HCl.H₂O: C, 42.30; H, 4.73; N, 16.44; H₂O, 5.29. FOUND: C, 42.40; H, 4.78; N, 16.24; H₂O, 5.18.

EXAMPLE III

N-(2,6-Dimethylphenyl)-N'-(1,4,5,6-tetrahydropyrimidin-2-yl)urea Monohydrochloride Hydrate (10:10:11)

A mixture of 8.13 g (0.060 mol) of 2-amino-1,4,5,6-tetrahydropyrimidine hydrochloride, 5.0 g (0.0625 mol) of 50% NaOH and 75 ml of THF was stirred for 0.5 hours at room temperature and then 10.0 g Na₂SO₄ was added. After stirring for 0.5 hours, a solution of 5.89 g (0.040 mol) of 2,6-dimethylphenyl isocyanate in 50 ml of THF was added over a period of 0.5 hours. After stirring for 1 hour, the reaction mixture was diluted with 100 ml of CH₂Cl₂, filtered, the filtrate evaporated in vacuo and the residue dissolved in 25 ml of 10% HCl and 50 ml of H₂O with warming. After filtration through a pad of diatomaceous earth, chilling in ice gave the crystalline hydrochloride which was recrystallized from cold H₂O affording 8.78 g (55%). This material was dried in vacuo (20° C., 5 mm Hg) to constant weight giving N-(2,6-dimethylphenyl)-N'-(1,4,5,6-tetrahydropyrimidin-2-yl)urea monohydrochloride hydrate (10:10:11); m.p. (110) 214.5°–216.5° C. dec.; IR (CHCl₃) 3226, 1710, 1676, 1641 cm⁻¹; UV max. (MeOH) 270 shl (ε1,000) and 233 nm (ε18,300).

ANAL. Calcd. for C₁₃H₁₈N₄O.HCl.1.1 H₂O: C, 51.60; H, 7.06; N, 18.52; H₂O, 6.55. FOUND: C, 51.68; H, 7.23; N, 18.53; H₂O, 6.49.

EXAMPLE IV

N-(2,6-Dibromo-4-fluorophenyl)-N'-(1,4,5,6-tetrahydropyrimidin-2-yl)urea Monohydrochloride A mixture of 8.14 g (0.060 mol) of 2-amino-1,4,5,6-tetrahydropyrimidine hydrochloride 6.0 g (0.075 mol) of 50% NaOH and 75 ml of THF was stirred at room temperature for 0.5 hours and then 10.0 g Na₂SO₄ was added. After stirring for 0.5 hours, a solution of 11.8 g (0.040 mol) of 2,6-dibromo-4-fluorophenyl isocyanate in 70 ml of THF was added over a period of 0.75 hours. After stirring for an additional 2 hours, the product THF suspension was decanted and filtered. The filtrate was evaporated in vacuo and the residue recrystallized from THF. The recrystallized material was combined with the filter cake and dissolved in a hot mixture of 25 ml of 10% HCl and 175 ml of H₂O. The hot solution was filtered through a pad of diatomaceous earth, then chilled in ice. The resulting crystals were filtered, washed with a minimum of ice H₂O and dried in air. Further drying in vacuo (50° C., 5 mm Hg) to constant weight afforded 10.70 g (62%) of pure N-(2,6-dibromo-4-fluorophenyl)-N-(1,4,5,6-tetrahydropyrimidin-2-yl)urea monohydrochloride; m.p. 221°–223° C. dec.; IR(KBr) 3242, 1705, 1676, 1639 cm⁻¹; UV max (MeOH) 277 infl (ε1,000) and 228 nm (ε27,900).

ANAL. Calcd. for $C_{11}H_{11}Br_2FN_4O \cdot HCl$: C, 30.69; H, 2.81; N, 13.01. FOUND: C, 3080; H, 2.61; N, 13.01.

EXAMPLE V

N-(2-Chloro-6-Methylphenyl)-N'-(1,4,5,6-tetrahydropyrimidin-2-yl)urea Monohydrochloride Hemihydrate A mixture of 8.14 g (0.060 mol) of 2-amino-1,4,5,6-tetrahydropyrimidine hydrochloride, 6.0 g (0.075 mol) of 50% NaOH and 75 ml of THF was stirred for 0.5 hours at room temperature and then 15 g $Na_2SO_4$ was added. After stirring for 0.5 hours, a solution of 6.70 g (0.040 mol) of 2-chloro-6-methylphenyl isocyanate in 50 ml of THF was added over a period of 0.5 hours. After stirring for 1 hour, the reaction mixture was filtered, the filtrate evaporated in vacuo and the residue dissolved in 25 ml of 10% HCl and 25 ml of $H_2O$ with warming. After filtration through diatomaceous earth chilling in ice gave the crystalline hydrochloride which was recrystallized from cold $H_2O$ after treatment with charcoal affording 7.15 g (59%). This material was dried in vacuo (20° C., 5 mm Hg) to constant weight to give 7.11 g (59%) of pure N-(2-chloro-6-methylphenyl)-N'-(1,4,5,6-tetrahydropyrimidin-2-yl)urea monohydrochloride hemihydrate, m.p. (190) 215°–220° C. melts, then forms a new solid; m.p. 243°–245° C.; $IR(CHCl_3)$ 3224, 1713, 1677, 1641, 1543 $cm^{-1}$; UV max. (MeOH) 236 (16,200) and 217 nm infl (21,500).

ANAL. Calcd. for $C_{12}H_{15}ClN_4O \cdot HCl \cdot 0.5H_2O$: C, 46.17; H, 5.49; N, 17.94; $H_2O$, 2.89. FOUND: C, 46.21; H, 5.53; N, 17.75; $H_2O$, 3.14.

EXAMPLE VI

According to the teachings of Examples I–V, the following compounds are prepared:
1. N-(2,6-Dimethoxyphenyl)-N'-(1,4,5,6-tetrahydropyrimidin-2-yl)urea and its monohydrochloride hydrate; m.p. 176°–178° C. dec.; 210°–212° C.
2. N-(2-Chloro-6-trifluoromethylphenyl)-N'-(1,4,5,6-tetrahydropyrimidin-2-yl)urea and acid addition salts (solvates, hydrates).
3. N-(2,6-bis-Trifluoromethylphenyl)-N'-(1,4,5,6-tetrahydropyrimidin-2-yl)urea and acid addition salts.
4. N-(2-Methyl-6-trifluoromethylphenyl)-N'-(1,4,5,6-tetrahydropyrimidin-2-yl)urea and acid addition salts.
5. N-(2,6-Dibromophenyl)-N'-(1,4,5,6-tetrahydropyrimidin-2-yl)urea and acid addition salts.
6. N-(2,6-Difluorophenyl)-N'-(1,4,5,6-tetrahydropyrimidin-2-yl)urea and acid addition salts.
7. N-(2-Bromo-6-chlorophenyl)-N'-(1,4,5,6-tetrahydropyrimidin-2-yl)urea and acid addition salts.
8. N-(2-Chloro-6-fluorophenyl)-N'-(1,4,5,6-tetrahydropyrimidin-2-yl)urea and acid addition salts.
9. N-(2-Bromo-6-methylphenyl)-N'-(1,4,5,6-tetrahydropyrimidin-2-yl)urea and acid addition salts.
10. N-(2-Chloro-6-methoxyphenyl)-N'-(1,4,5,6-tetrahydropyrimidin-2-yl)urea and acid addition salts.

EXAMPLE VII 1,000 hard gelatin capsules, each containing 200 milligrams of N-(2,6-dichlorophenyl)-N'-(1,4,5,6-tetrahydropyrimidin-2-yl)urea are prepared from the following formulation:

| | Grams |
|---|---|
| N—(2,6-Dichlorophenyl)- | 200 |
| N'—(1,4,5,6-tetrahydropyrimidin-2-yl)urea | |
| Starch | 250 |
| Lactose | 750 |
| Talc | 250 |
| Calcium Stearate | 10 |

A uniform mixture of the ingredients is prepared by blending and employed to fill two-piece hard gelatin capsules. The capsules are suitable to be orally administered to subjects with functional bowel disorders.

EXAMPLE VIII

Gelatin capsules are prepared as described in Example VI except that in the formulation, 400 grams of N-(2,6-dibromophenyl)-N'-(1,4,5,6-tetrahydropyrimidin-2-yl)urea is employed as active agent providing capsules containing 400 milligrams of N-(2,6-dibromophenyl)-N'-(1,4,5,6-tetrahydropyrimidin-2-yl)urea.

EXAMPLE IX

Gelatin capsules are prepared as described in Example VIII except that N-(2-chloro-6-methyl)-N'-(1,4,5,6-tetrahydropyrimidin-2-yl)urea is employed as the active agent.

EXAMPLE X

Gelatin capsules are prepared as described in Example VIII except that N-(2,6-dimethylphenyl)-N'-(1,4,5,6-tetrahydropyrimidin-2-yl)urea is employed as the active agent.

EXAMPLE XI 1,000 compressed tablets, each containing 500 milligrams of N-(2-chloro-6-methylphenyl)-N'-(1,4,5,6-tetrahydropyrimidin-2-yl)urea are prepared from the following formulation:

| | Grams |
|---|---|
| N—(2-Chloro-6-methylphenyl)- N'—(1,4,5,6-tetrahydropyrimidin-2-yl)urea | 500 |
| Starch | 750 |
| Dibasic calcium phosphate hydrous | 5,000 |
| Calcium stearate | 2.5 |

The finely powdered ingredients are mixed well and granulated with 10 percent starch paste. The granulation is dried and compressed into tablets using starch as a disintegrant and calcium stearate as a lubricant.

I claim:
1. A method for relieving the symptoms associated with irritable bowel syndrome which comprises administering to an animal having said syndrome a therapeutically-effective amount of a urea compound selected from the group consisting of (a) an N-(phenyl)-N'-(1,4,5,6-tetrahydropyrimidin-2-yl)urea, having the formula:

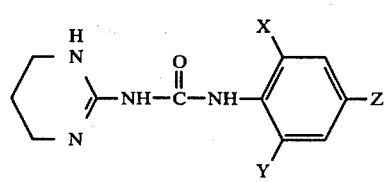

wherein Z is H or F; X and Y are each independently selected from the group consisting of Br, Cl, F, CH₃, CF₃, and OCH₃; and (b) a pharmaceutically-acceptable salt thereof.

2. A method for relieving the symptoms associated with irritable bowel syndrome which comprises administering to an animal having said syndrome from about 1 to 500 milligrams per unit dose of an N-(phenyl)-N'-(1,4,5,6-tetrahydropyrimidin-2-yl)urea compound represented by the formula:

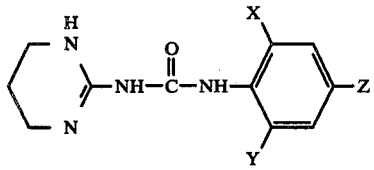

wherein Z is H; X and Y are each independently selected from the group consisting of Br, Cl, CH₃, and CF₃; and pharmaceutically-acceptable salts thereof.

3. A method according to claim 2 in which the urea compound is N-(2,6-dichlorophenyl)-N'-(1,4,5,6-tetrahydropyrimidin-2-yl)urea; and pharmaceutically-acceptable salts thereof.

4. A method according to claim 2 in which the urea compound is N-(2,6-dimethylphenyl)-N'-(1,4,5,6-tetrahydropyrimidin-2-yl)urea; and pharmaceutically-acceptable salts thereof.

5. A method according to claim 2 in which the urea compound is N-(2,6-dibromo)-N'-(1,4,5,6-tetrahydropyrimidin-2-yl)urea; and pharmaceutically-acceptable salts thereof.

6. A method according to claim 2 in which the urea compound is N-(2-chloro-6-methylphenyl)-N'-(1,4,5,6-tetrahydropyrimidin-2-yl)urea; and pharmaceutically-acceptable salts thereof.

7. A method for the treatment of diarrhea in mammals which comprises the administering thereto a therapeutically effective amount of a urea compound of the formula:

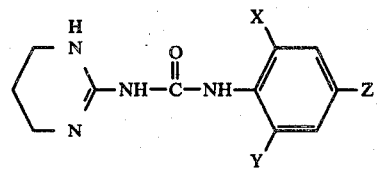

wherein Z is H or F; X is selected from the group consisting of Br, Cl, CH₃ and CF₃; and Y is selected from the group consisting of Br, Cl, CH₃ and CF₃; and the pharmaceutically-acceptable acid addition salts thereof.

8. A method according to claim 7 in which the urea compound is N-(2,6-Dichlorophenyl)-N'-(1,4,5,6-tetrahydropyrimidin-2-yl)urea and pharmaceutically-acceptable salts thereof.

9. A method according to claim 7 in which the urea compound is N-(2-chloro-6-methylphenyl)-N'-(1,4,5,6-tetrahydropyrimidin-2-yl)urea and pharmaceutically-acceptable salts thereof.

10. A method according to claim 7 in which the urea compound is (N-2,6-Dimethylphenyl)-N'-(1,4,5,6-tetrahydropyrimidin-2-yl)urea and pharmaceutically-acceptable salts thereof.

11. N-(2,6-Dichlorophenyl)-N'-(1,4,5,6-tetrahydropyrimidin-2-yl)urea and pharmaceutically-acceptable salts thereof.

12. N-(2-chloro-6-methylphenyl)-N'-(1,4,5,6-tetrahydropyrimidin-2-yl)urea and pharmaceutically-acceptable salts thereof.

* * * * *